United States Patent [19]

Miyazaki et al.

[11] Patent Number: 5,064,731
[45] Date of Patent: Nov. 12, 1991

[54] DENTAL PROSTHESES

[75] Inventors: Takashi Miyazaki; Takashi Inamochi; Masaaki Kitamura; Shohei Hayashi, all of Tokyo, Japan

[73] Assignee: G-C Dental Industrial Corp., Tokyo, Japan

[21] Appl. No.: 496,943

[22] Filed: Mar. 21, 1990

[30] Foreign Application Priority Data

Mar. 29, 1989 [JP] Japan ................................ 1-74935

[51] Int. Cl.$^5$ ............................................. B32B 15/00
[52] U.S. Cl. ................................... 428/698; 106/1.13; 106/1.14; 106/1.26; 420/585; 433/206; 433/207; 433/209; 433/212.1; 433/228.1; 428/457; 428/469; 428/472; 428/701; 428/688; 428/702; 428/704
[58] Field of Search .................... 433/207, 209, 212.1, 433/228.1, 226, 206; 106/1.13, 1.14, 1.26; 428/457, 469, 698, 704, 472, 701, 702, 688; 420/585

[56] References Cited

U.S. PATENT DOCUMENTS 4,321,042  3/1982  Scheicher ...................... 433/212.1
4,327,014  4/1982  Kawahara et al. ............. 433/228.1
4,451,236  5/1984  Tarasov et al. .................. 433/207
4,468,251  8/1984  Hausselt et al. ................. 106/1.14
4,556,389  12/1985 Ueno et al. ...................... 428/469

FOREIGN PATENT DOCUMENTS 2023953  1/1990  Japan .
2023955  1/1990  Japan .

Primary Examiner—Patrick J. Ryan
Assistant Examiner—Archene Turner
Attorney, Agent, or Firm—Oblon, Spivak, McClelland, Maier & Neustadt

[57] ABSTRACT

A dental prosthesis comprises an inner layer portion and an outer layer portion. The outer layer portion is a dental porcelain material, while the inner layer portion is a sintered product which, after sintering, is composed of:

(i) 40 to 95% by weight of one or (two or) more electric conductive ceramic materials selected from the group consisting of nitride ceramics, boride ceramics and carbide ceramics, all having a specific electric resistance of $10^{-1}$ Ω·cm or below, and (ii) 5 to 60% by weight of the following (A) and/or (B):
  (A) a dental porcelain material, and
  (B) one or (two or) more metals selected from the group consisting of Ti, Zr, Au, Pt, Pd, Ag, In and Sn.

6 Claims, No Drawings

DENTAL PROSTHESES

BACKGROUND OF THE INVENTION

1. Field of the Invention

The present invention relates to a dental prosthesis suitable for the restoration of the teeth with crowns, bridges, etc.

2. Prior Art

Heretofore, dental prostheses placed in the oral cavity such as crowns or bridges have been required to possess the following properties:
1. Safety in use.
2. Biocompatibility to intra-oral tissue.
3. Corrosion resistance to intr-oral environment (chemical stability).
4. Strength in intra-oral environment (dynamic stability).
5. Physical durability in intra-oral environment.
6. Fitness to abutment teeth.
7. Esthetics.

Of these properties, weight has recently been placed on esthetics. For that reason, frequent use has been made of dental prostheses made of the so-called metal baked porcelain including an inner layer portion prepared with an alloy to be baked with porcelain by the lost wax casting technique and an outer layer portion formed of dental porcelain baked to the inner layer portion or dental prostheses made of the so-called all-ceramics including an inner layer portion prepared by building dental porcelain up on a metal foil or refractory material and baking it, and an inner layer portion to which the outer layer portion of the dental porcelain is baked. Comparatively lately, further dental prostheses have been developed, including an inner layer portion made of an electric conductive sintered ceramic product by the ram-type electric discharge machining and an outer layer portion to which dental porcelain is baked.

However, the dental prostheses made of the metal baked porcelain are disadvantageous in that they may give rise to a discoloration of the gingival margin in the oral cavity or become poor in corrosion resistance when a base metal alloy is used for the inner layer portions, and pose a problem of safety, e.g., an allergic problem due to alloy components. Another problem is that, prepared by the lost wax casting process, the inner layer portions often fail to possess sufficient strength due to casting defects such as porosities, or become so poor in the accuracy of fitness to abutment teeth, as occurring with a bridge applied across a number of teeth, that no sufficient accuracy of fitness to abutment teeth can be obtained even by relying upon soldering. The application of a noble metal alloy to the inner layer portions has the disadvantage of causing a thermal deformation in thin regions such as marginal regions.

On the other hand, the dental prostheses made of ceramics in their entirety have an inner layer portion prepared by the building-up and baking of dental porcelains. However, they have the disadvantages that they are inferior in the accuracy of fitness to abutment teeth because the shrinkage of dental porcelain is increased upon baking. They can neither be applied in the form of such specific dental prostheses as bridges because general dental porcelain has reduced or limited strength, although alumina porcelain is of higher strength.

Recently developed dental prostheses including inner layer portions formed of an electric conductive sintered ceramic product of titanium boride have the advantages that the inner layer portions excel in the accuracy of fitness to abutment teeth because of being formed by the ram-type electric discharge machining, are so much higher in strength than dental porcelain, as expressed in terms of a bending strength of about 700 MPa and a fracture toughness value of about 4.0 MN/m$^3$ $^2$, that they can be used for an inner layer portion of a bridge applied across a number of teeth, and show reduced or limited deformation upon the baking of porcelain. However, they have the disadvantages that no sufficient bonding strength is obtained because they can hardly be diffused between the electric conductive sintered ceramic product and porcelain baked as an outer layer portion, and their coefficient of thermal expansion is as low as 4 to $6 \times 10^{-6}/°$ C. so that it is impossible to use as an outer layer portion porcelain to be baked with a metal, which has a coefficient of thermal expansion of, e.g., 10 to $20 \times 10^{-6}/°$ C., thus making it necessary to select and use a dental porcelain material having a low coefficient of thermal expansion. In some cases, the dental porcelain baked as the outer layer portion may crack due to a difference in the coefficient of thermal expansion. Additionally, the electric conductive sintered ceramic product of titanium boride involves difficulty in its shape modification because of their hardness Hv being as high as 3350.

SUMMARY OF THE INVENTION

With the above problems in mind, the present inventors have made an intensive study of dental prostheses suitable for the restoration of teeth such as crowns and bridges, and have consequently developed a dental prosthesis comprising an inner layer portion and an outer layer portion, characterized in that said inner layer portion is a sintered product which, after sintering, is composed of:

(i) 40 to 95% by weight of one or (two or) more electric conductive ceramic materials selected from nitride ceramics, boride ceramics and carbide ceramics, all having a specific electric resistance of $10^{-1} \Omega \cdot cm$ or below, and (ii) 5 to 60% by weight of the following (A) and/or (B):

(A) a dental porcelain material, and
(B) one or (two or) more metals selected from the group consisting of Ti, Zr, Au, Pt, Pd, Ag, In and Sn, and said outer layer is a dental porcelain material.

Thus, the present invention provides a dental prosthesis suitable for the restoration of the teeth such as a crown or bridge, which makes the best use of the advantages of conventional dental prostheses each including an inner layer portion of a sintered product which can be machined by the electric discharge machine, i.e., those whose accuracy of fitness to abutment teeth is improved and their strength is high, and gives a solution to such problems as mentioned above.

DETAILED EXPLANATION OF THE INVENTION

Dental porcelain is so much lower in melting point and hardness than electric conductive ceramics that it can serve to reduce the temperature at which sintered products are prepared and can lower the hardness of the sintered products, when comparing with the sole use of electric conductive ceramics. When a sintered product consisting of electric conductive ceramics and dental porcelain is used for an inner layer portion, dental porcelain baked as an outer layer portion is so fused to the dental porcelain in the inner layer portion that a dental prosthesis having improved bonding strength can be obtained. The obtained inner layer portion has also its coefficient of thermal expansion close to that of the dental porcelain used for the outer layer portion. It is thus unlikely that the dental porcelain of the outer layer portion may crack. If required, the form of dental prostheses may be easily modified with a dental abrasive material because of their hardness being reduced to a suitable level.

Metals are so lower in melting point and hardness than electric conductive ceramics that they can be sintered at lower temperature when comparing with the sole use of electric conductive ceramics, thus producing an effect upon a lowering of the hardness of the sintered products and improvements in the electric discharge machining properties thereof. When a sintered product consisting of electric conductive ceramics and metal is used for an inner layer portion, diffusion takes place between dental porcelain baked as an outer layer portion and the metal in the inner layer portion, thus yielding a dental prosthesis having improved bonding strength. Moreover, since the coefficient of thermal expansion of the inner layer portion can be suitably determined depending upon the type and proportion of the metal contained in the sintered product, it can be made close to the coefficient of thermal expansion of the dental porcelain used as the outer layer portion. It is thus unlikely that the dental porcelain baked as the outer layer portion may crack. If required, the form of dental prostheses may be easily modified with a dental abrasive material because of the hardness of their inner layer portions is reduced to a suitable level.

It is understood that the incorporation of both dental porcelain and metal into the sintered produces similar effects as those obtained by the separate incorporation of dental porcelain or metal.

As the electric conductive ceramic materials contained in the sintered products, use may be made of one or (two or) more materials selected from nitride ceramics, boride ceramics and carbide ceramics, all having a specific electric resistance of $10^{-1} \Omega \cdot cm$ or below. These electric conductive ceramics may include nitride systems such as TiN, ZrN, TaN, VN and NbN; boride systems such as $TiB_2$, $ZrB_2$, $TaB_2$, $MoB_2$, $CrB_2$, $NbB_2$ and WB; and carbide systems such as TiC, ZrC, VC, NbC, TaC and WC. Among others, preference is given to nitride ceramics TiN and ZrN, partly because they are much safe in use and partly because they make it easy to regulate the color harmony of dental porcelain baked as an outer layer portion as they assume a gold color. Suitably, the proportion of the electric conductive ceramics in the sintered products is in a range of 40 to 95% by weight. At below 40% by weight, the sintered products will fail to produce their desirable properties. An amount exceeding 95% by weight is not desirable, since the effect of the sintered products is substantially equal to that obtained with electric conductive ceramics itself.

As the dental porcelain materials contained in the sintered products, use may be made of any one of pocelain materials generally used in dentistry such as a low-melting porcelain material (borosilicate glass), a high-melting porcelain material (feldspar porcelain), an alumina porcelain material (high alumina borosilicate glass) and a metal bonded porcelain (porcelain to be baked with a metal). However, preference is given to a porcelain material similar to that used for the outer layer portion. As the metals contained in the sintered products, preference is given to one or two or more metals selected from the group consisting of Ti, Zr, Au, Pt, Pd, Ag, In and Sn which are much safe in use and excel in corrosion resistance.

After sintering, such dental porcelain materials and metals preferably account for 5 to 60% by weight of the sintered product. At below 5% by weight, they will not sufficiently produce their own effects. In an amount exceeding 60% by weight, the electrical conductivity of the sintered product is so reduced when dental porcelain is incorporated that its electric discharge machining becomes difficult, while the sintered product hardly functions as electric conductive ceramics when metals are incorporated.

It is understood that like conventional electric conductive sintered ceramic products, the sintered products may be formed into blocks by processing a uniform mixture of electric conductive ceramic powders, dental porcelain and metal powders by electric current sintering, sintering at normal pressure, hot forming, hot isotropic pressing, reaction sintering, liquid-phase sintering, atmospheric sintering, etc. Preferably, however, the sintered products should be previously formed into the so-called near net shape close to that of the desired inner layer portion. This is because the amount of the material to be machined by electric discharge machining and the consumption of the electrodes are both much reduced, thus doing much to reductions in the production time and processing cost. More preferably, the near net shape type of sintered product may be formed into a double layer structure in which it contains larger amounts of dental porcelain and metal on its side to be baked with dental porcelain as an outer layer portion and no, or smaller amounts of, dental porcelain and metal on its opposite side (to contact abutment teeth), making it a double structure or giving it a step-down amounts.

As is the case with the dental porcelain contained in the inner layer portion, low- and high-melting, alumina and metal bonded porcelain materials generally employed in dentistry may be used for the dental porcelain applied as the outer layer portion.

According to such conventional procedures as used to prepare dental prostheses in which electric conductive sintered ceramic products are used for the inner layer portions, the dental prostheses of the present invention may be prepared by mounting two electrodes on an electric discharge machine, each of said electrodes being precisely transferred thereon with the occlusal or abutment teeth side of a prototype for inner layer portions, then positioning a sintered product between both the electrodes to apply a pulse current thereto for electric discharge machining, thereby making an inner layer portion, and finally placing dental porcelain on the obtained inner layer portion in the order of opaque, dentin and enamel and baking it thereto, thereby making an outer layer portion.

EXAMPLES

The present invention will now be explained specifically but not exclusively with reference to the examples. Prepared sintered products composed of such components as tabulated (in weight %), after sintering, with which dental prostheses for bridges were made. For comparison, such bridges were tested in the following manners.

Preparation of Sintered Products

In Examples 1 to 6 and Comparative Example 2, sintered products composed of such components as tabulated were prepared with electric conductive ceramic powders (available from Nippon Shin-Kinzoku K.K.), dental porcelain powders and metal powders by electric current sintering under the conditions of 4000 A, 1600° to 2000° C. and 30 to 60 minutes. In Comparative Example 1, a commercially available sintered product (Nippon Tungsten K.K.) was used.

Preparation of Dental Prostheses

Using the sintered products formed into a block or near net shape according to the above procedures for preparing sintered products, dental prostheses for bridges were made in the following manners.

(1) Occlusal and abutment teeth electrodes, transferred thereon with a prototype for the inner layer portion of a dental bridge prosthesis by electroforming, were attached to an electric discharge machine (special precision machine by I.J.R. Co., Ltd.), and the above sintered product was positioned between both the electrodes.

(2) For electric discharge machining, a pulse current of 2 to 16 A in pulse height, 4 to 100 μsec in pulse on time and 6 to 400 μsec in pulse off time was impressed on the electric discharge machine to form the sintered product into the same shape as the prototype for the inner layer portion.

(3) According to the maker's instructions, the dental porcelain as tabulated was repeatedly placed and sintered on the obtained inner layer portion in the order of opaque, enamel and dentin to form an outer layer portion baked thereto.

Physical Properties and Testing Manners (1) Color tone: visually observed.

(2) Hardness: After each sintered product was polished on its surface with emery paper, the hardness of the polished surface was measured with a microhardness tester in terms of micro-Vickers hardness.

(3) Compression strength: measured with a columnar sintered sample ($\phi 3 \times 6$ mm) by a universal testing machine.

(4) Coefficient of thermal expansion: found by a curve of thermal expansion of a columnar sintered sample ($\phi 3 \times 8$ mm) obtained by plotting measurements by thermal expansion meter under constant micro load during heating from room temperature up to 1000° C. and cooling.

(5) Bonding strength: measured with a columnar sintered sample ($\phi 3 \times 8$ mm) baked thereto with dental porcelain according to the maker's instructions by pushing shear bond strength testing with a universal testing machine.

(6) Electric discharge machining property: measured in terms of the machining rate in mg/min, consumption % of electrode and surface roughness (Ra in μm) of a sintered sample, when machined by electric discharge machining with a columnar copper electrode of 7 mm in diameter.

(7) Cracking of dental porcelain: visually observed when dental porcelain was placed and sintered as an outer layer portion on an inner layer portion for baking thereto.

(8) Accuracy of fitness to abutment teeth: measured while the prepared dental prosthesis was mounted on a teeth model.

TABLE

| Inner layer | Example 1 | Example 2 | Example 3 | Example 4 | Example 5 | Example 6 | Comparative Example 1 | Comparative Example 2 |
|---|---|---|---|---|---|---|---|---|
| Electric conductive ceramic | | | | | | | | |
| TiN | 70 | 60 | — | 80 | 70 | — | — | 100 |
| ZrN | — | — | 50 | — | — | — | — | — |
| TiB$_2$ | — | — | — | — | — | 70 | — | — |
| NbC | — | — | 20 | — | — | — | 100 | — |
| Dental porcelain | | | | | | | | |
| Alumina porcelain (Brandname: VITA DUR-N made by VITA Co.) | — | — | 30 | 20 | 15 | — | — | — |
| Metal bonded porcelain (Brandname: VITA VMK68 made by VITA Co.) | 30 | 20 | — | — | — | — | — | — |
| Metal | | | | | | | | |
| Ti | — | — | — | — | 15 | 30 | — | — |
| Au | — | 15 | — | — | — | — | — | — |
| In | — | 5 | — | — | — | — | — | — |

| Outer layer | Metal bonded porcelain (Brandname: VITA VMK68 made by VITA Co.) | | Alumina porcelain (Brandname: VITA DUR-N made by VITA Co.) | | | | Alumina porcelain (Brandname: VITA DUR-N made by VITA Co.) | |
|---|---|---|---|---|---|---|---|---|
| Items of evaluation | | | | | | | | |
| Colour tone | Gold | Gold | Light brown | Gold | Gray | Gray | Black | Gold |
| Hardness (Hv) | 782 | 620 | 715 | 750 | 730 | 870 | 3350 | 920 |
| Compression strength (MPa) | 1030 | 910 | 950 | 1080 | 1020 | 1050 | 1400 | 1130 |
| Coefficient of thermal expansion ($\times 10^{-6}$/°C.) | 12.0 | 13.5 | 7.2 | 7.9 | 7.4 | 7.1 | 6.3 | 8.3 |
| Bonding strength (kgf/cm$^2$) | 200 | 250 | 220 | 270 | 262 | 210 | 100 | 190 |
| Electric discharge machining property | | | | | | | | |
| Machining rate (mg/min) | 12.5 | 14.2 | 12.8 | 14.4 | 14.8 | 13.0 | 15.0 | 25.0 |
| Consumption % of | 1.5 | 1.4 | 1.4 | 1.7 | 1.8 | 1.5 | 3.4 | 1.4 |

TABLE-continued

| electrode (%) | | | | | | | | |
|---|---|---|---|---|---|---|---|---|
| Surface roughness (Ra μm) | 1.23 | 1.22 | 1.28 | 1.20 | 1.28 | 1.18 | 1.20 | 1.24 |
| Cracking of dental porcelain | None | None | None | None | None | None | Much | Less |
| Accuracy of fitness to abutment teeth | Good | Good | Good | Good | Good | Good | Good | Good |

The results set out in the table reveal:

the sintered products used for the inner layer portions according to the examples are higher in terms of bonding strength than the electric conductive sintered ceramic product of the comparative example, since they contain dental porcelain and metal;

their coefficients of thermal expansion are regulated to a suitable value and the outer layer portions of dental porcelain baked are unlikely to crack;

their hardness is reduced to a suitable level and their form can be modified with a dental abrasive material such as a diamond wheel, and their compression strength is sufficiently comparable to that obtained with the sole use of conventional electric conductive ceramics, although their hardness drops to a suitable level. It is also found that the present sintered products are made nearly comparable to conventional electric conductive ceramics in terms of electric discharge machining property by the selection of machining conditions, and are as much improved in the accuracy of fitness to abutment teeth as conventional dental prostheses using electric conductive ceramics.

As mentioned above, the dental prostheses of the present invention show sufficient strength and improved fitness, even when applied to bridges attached across a number of teeth, have their inner and outer layer portions bonded together so firmly that the outer layer portions are unlikely to crack, and can be modified in shape with a dental abrasive material. In addition, they can satisfactorily meet such properties as heretofore required and mentioned below:

(1) Safety in use.
(2) Biocompatibility to intra-oral tissue.
(3) Corrosion resistance to intra-oral environment (chemical stability).
(4) Strength in intra-oral environment (dynamic stability).
(5) Physical durability in intra-oral environment.
(6) Fitness to abutment teeth.
(7) Esthetics.

What is claimed is:

1. A dental prosthesis comprising an inner layer portion and an outer layer portion, characterized in that:
    said inner layer portion is a sintered product which, after sintering, is composed of:
    (i) 40 to 95% by weight of one or more electric conductive ceramic materials selected from the group consisting of nitride ceramics, boride ceramics and carbide ceramics, all having a specific electric resistance of $10^{-1}\Omega\cdot cm$ or below, and
    (ii) 5 to 60% by weight of at least one of the following (A) and (B):
        (A) a dental porcelain material, and
        (B) one or more metals selected from the group consisting of Ti, Zr, Au, Pt, Pd, Ag, In and Sn,
    and said outer layer portion is a dental porcelain material.

2. The dental prosthesis of claim 1 wherein the electric conductive ceramic material of the inner layer is selected from the group consisting of TiN, ZrN, $TiB_2$ and NbC.

3. The dental prosthesis of claim 1 wherein the dental porcelain material of the inner layer is selected from the group consisting of alumina porcelain and metal bonded porcelain.

4. The dental prosthesis of claim 1 wherein the metal of the inner layer is selected from the group consisting of Ti, Au and In.

5. The dental prosthesis of claim 1 wherein the dental porcelain material of the outer layer is selected from the group consisting of alumina porcelain and metal bonded porcelain.

6. The dental prosthesis of claim 1 wherein the content of said one or more electric conductive ceramic materials is 60 to 80% by weight.

* * * * *